United States Patent
Dickner et al.

(10) Patent No.: US 9,969,513 B2
(45) Date of Patent: May 15, 2018

(54) DEVICE AND METHOD FOR STERILIZATION OF PACKAGING CONTAINERS

(71) Applicant: TETRA LAVAL HOLDINGS & FINANCE S.A., Pully (CH)

(72) Inventors: Jonas Dickner, Påarp (SE); Håkan Mellbin, Hörby (SE); Roger Lindgren, Sövde (SE); Fredrik Hansen, Bjärred (SE)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 0 days. days.

(21) Appl. No.: 15/115,537

(22) PCT Filed: Jan. 16, 2015

(86) PCT No.: PCT/EP2015/050741
§ 371 (c)(1),
(2) Date: Jul. 29, 2016

(87) PCT Pub. No.: WO2015/113835
PCT Pub. Date: Aug. 6, 2015

(65) Prior Publication Data
US 2017/0183114 A1    Jun. 29, 2017

(30) Foreign Application Priority Data
Jan. 31, 2014    (SE) ...................................... 1450101

(51) Int. Cl.
*A61L 9/00* (2006.01)
*A61L 2/00* (2006.01)
(Continued)

(52) U.S. Cl.
CPC .............. *B65B 55/08* (2013.01); *A61L 2/087* (2013.01); *A61L 2/20* (2013.01); *B65B 55/10* (2013.01);
(Continued)

(58) Field of Classification Search
CPC ........ A61L 2/18; A61L 2202/23; A61L 2/087; H01J 37/30; H01J 2237/06366
(Continued)

(56) References Cited

U.S. PATENT DOCUMENTS 5,612,588 A    3/1997    Wakalopulos
6,139,796 A    10/2000   Kristiansson et al.
(Continued)

FOREIGN PATENT DOCUMENTS

EP    1 982 920 A1    10/2008
EP    2 491 955 A1    8/2012
(Continued)

OTHER PUBLICATIONS

U.S. Appl. No. 15/115,509, filed Jul. 29, 2016, Dickner et al.
(Continued)

*Primary Examiner* — Monzer R Chorbaji
(74) *Attorney, Agent, or Firm* — Buchanan Ingersoll & Rooney PC (57) ABSTRACT

The invention relates to a device for sterilization of the interior surface of packaging containers with electron beam, comprising an emitter provided with an electron exit window. The emitter is adapted to emit charge carriers, such as electrons, through the electron exit window, said electrons forming an electron cloud. The device comprises at least one outlet adapted to provide a flow of sterile gaseous medium adapted to maintain a local aseptic zone around at least an emitter portion including the electron exit window, thus preventing any flow of medium from outside the local
(Continued)

aseptic zone from coming into the local aseptic zone. The invention also relates to a method.

19 Claims, 10 Drawing Sheets

(51) Int. Cl.
| | | |
|---|---|---|
| *C01B 25/00* | (2006.01) | |
| *G01N 23/00* | (2006.01) | |
| *B65B 55/08* | (2006.01) | |
| *A61L 2/08* | (2006.01) | |
| *A61L 2/20* | (2006.01) | |
| *B65B 55/10* | (2006.01) | |
| *B67C 7/00* | (2006.01) | |

(52) U.S. Cl.
CPC ......... *B67C 7/0073* (2013.01); *A61L 2202/23* (2013.01)

(58) Field of Classification Search
USPC ......... 422/4, 32, 186.05, 292, 306; 250/427, 250/455.11, 492.3; 204/157.44
See application file for complete search history.

(56) References Cited

U.S. PATENT DOCUMENTS

| | | |
|---|---|---|
| 6,140,657 A | 10/2000 | Wakalopulos et al. |
| RE39,657 E | 5/2007 | Wakalopulos et al. |
| 2008/0138243 A1* | 6/2008 | Kristiansson ........... A61L 2/087 422/23 |
| 2009/0045350 A1 | 2/2009 | Humele et al. |
| 2009/0090086 A1 | 4/2009 | Lindblad et al. |
| 2011/0012032 A1 | 1/2011 | Bufano et al. |
| 2012/0219455 A1 | 8/2012 | Meinzinger et al. |
| 2013/0015365 A1 | 1/2013 | Bufano et al. |

FOREIGN PATENT DOCUMENTS

| | | |
|---|---|---|
| EP | 2 746 174 A1 | 6/2014 |
| WO | WO 96/21238 A1 | 7/1996 |
| WO | WO 97/07024 A1 | 2/1997 |
| WO | WO 00/55884 A1 | 9/2000 |
| WO | WO 2007/024173 A1 | 3/2007 |
| WO | WO 2007/145561 A1 | 12/2007 |
| WO | WO 2014/095838 A1 | 6/2014 |

OTHER PUBLICATIONS

International Search Report (PCT/ISA/210) dated Mar. 10, 2015, by the European Patent Office as the International Searching Authority for International Application No. PCT/EP2015/050741.
Written Opinion (PCT/ISA/237) dated Mar. 10, 2015, by the European Patent Office as the International Searching Authority for International Application No. PCT/EP2015/050741.
International-Type Search Report (Form ITS/201) dated Sep. 15, 2014 for Application No. 1450101-9.

\* cited by examiner

DEVICE AND METHOD FOR STERILIZATION OF PACKAGING CONTAINERS

This invention relates to a device and method for sterilization of the interior surface of packaging containers with electron beam.

In the prior art different devices and methods for sterilizing packaging materials are known. One method widely used in the prior art is sterilization by means of gases and in particular by means of hydrogen peroxide. However, efforts are being made to reduce the use of chemicals when sterilizing containers. Therefore, devices and methods have also become known which sterilize material by means of ultraviolet radiation or electron beams. In general, there is provided an emitter that is adapted to emit charge carriers, in particular electrons, wherein the packaging material can be sterilized by the charge carriers. For this purpose the packaging material and the emitter or the emitters, respectively, are moved relatively to each other. However, when the emitter and the packaging material are moved relatively to each other, flows or streams of a medium, such as gas, are established in between. If these streams or flows comprise a medium, in particular air, that is not sterile or aseptic, there exists the risk that parts of the packaging material that have already been sterilized are re-infected by unsterile airstreams or -flows.

Therefore, it is an object of the current invention to provide a device for sterilization of the interior surface of packaging containers with electron beam, in which device a local aseptic zone is created which prevents any flow of medium from outside the local aseptic zone from coming into the local aseptic zone during and after the sterilization.

This object is achieved by means of a device according to claim 1 and a method according to claim 15. Additional advantages and features of embodiments of the current invention are defined in the dependent claims.

The device comprises an emitter provided with an electron exit window. Said emitter is adapted to emit charge carriers, such as electrons, through the electron exit window. Said electrons form an electron cloud. The device further comprises at least one outlet adapted to provide a flow of sterile gaseous medium adapted to maintain a local aseptic zone around at least an emitter portion including the electron exit window, thus preventing any flow of medium from outside the local aseptic zone from coming into the local aseptic zone.

The emitter portion has a first end connecting to the rest of the emitter and a second end comprising the electron exit window. The outlet is arranged such that the sterile gaseous medium is flowing along the emitter portion in a direction from the first end to the second end.

The packaging container is basically tube-shaped, and the opening is adapted to enable an insertion of the emitter into the packaging container. The packaging container is closed at its other end portion opposite the opening. The term "tube-shaped" comprises no limitations concerning the possible form of the cross-section of the packaging container. This means that the cross section can be round, rectangular, circular, polygonal and/or angular. The packaging container extends along an axis, and the cross section does not have to be constant along said axis.

The packaging container can for example be made of a plastic material such as for instance PET, or be made of a laminated carton material. With regard to the later a common type of laminated carton material are the ones comprising a core layer of paper or paperboard and one or more barrier layers of, for example, polymer material or aluminium foil. An increasingly common packaging type is the "carton bottle" manufactured in a filling machine in that packaging blanks of the above-described packaging laminate are formed and sealed as a sleeve. Said sleeve is closed in one end in that a top of thermoplastic material is injection moulded directly on the sleeve end portion. The sheets of packaging laminate may be cut from a magazine reel of packaging laminate.

Advantageously, the opening of the packaging container, e.g. the spout or a bottom of the packaging container, has to be big enough so that at least the emitter portion comprising the electron exit window can be passed through it, to sterilize in particular the interior surface of the packaging container. In one or more embodiments the emitter has a round, in particular a circular cross section that is basically constant. A diameter of the cross-section lies within a range of about 5-100 mm.

Sterilization is a term referring to any process that eliminates or kills microbial life, including transmissible agents such as for example fungi, bacteria, viruses and spores, which may be present on a surface of the packaging material or in a product. In the (food) packaging industry this is generally referred to as aseptic packaging, i.e. packaging sterilized products in sterilized packaging containers, i.e. keeping both the product and the packaging container free form living germs and microorganisms, so that the freshness of the product can be preserved without special cooling requirements, i.e. so that sterility can be maintained inside a packaging container although it is stored in ambient temperature. In this context the term "commercially sterile" is also commonly used and means in general the absence of microorganisms capable of growing in the food at normal non-refrigerated conditions at which the food is likely to be held during manufacture, distribution and storage. In this patent application the word "sterile" refers to a condition being at least commercially sterile.

As mentioned above, any flow of medium from outside the local aseptic zone is prevented from coming into the local aseptic zone. To stay sterilized, and not risking being re-infected, a sterilized surface and/or volume of air near a sterilized surface cannot have contact with non-aseptic or non-sterile medium/air. In this context it has to be clarified that the medium or the air, respectively, that is provided by the at least one outlet does not have to have a specific mixture. However, it has to be ensured that the medium or the mixture is aseptic or sterile.

In one or more embodiments the emitter and the packaging container are adapted to perform a movement relatively to each other such that the emitter portion is temporarily positioned inside the packaging container via an opening. The local aseptic zone is adapted to include the opening of the packaging container at least during the relative movement.

In one or more embodiments the emitter and the packaging container are adapted to perform the movement relatively to each other between first and second positions. The first position is a position in which the packaging container and the emitter are not engaged with each other, and the second position is a position in which the emitter portion is fully inserted into the packaging container, through the opening of the packaging container, for sterilization of the interior surface of the packaging container.

The second position should be deep enough located inside the packaging container so that sterilization of the inside of the packaging container is possible, especially the end of the packaging container located opposite the opening.

The term "relative movement between the emitter and the packaging container" comprises every possible movement arrangement. In one or more embodiments the emitter moves in relation to the packaging container (the packaging container being stationary along the axis). Alternatively, in one or more embodiments the packaging container moves towards and away from the emitter (the emitter being stationary along the axis). The emitter will hence be inserted into the packaging container in that the emitter is received in the packaging container. In other words, the packaging container will be moved to surround the emitter. Alternatively, in one or more embodiments, both the emitter and the packaging container are moved. Each performs a part of the relative movement.

In between the emitter and the packaging container there is formed a gap. The gap can have a constant size or thickness. However, it does not have to be constant. Its size can change when the emitter and the packaging container are moved relatively to each other. This means that the gap can get thicker and/or thinner when the emitter and the packaging container are moved relatively to each other. Inserting the emitter into the packaging container creates basically an outflow of medium out of the packaging container through the opening or through the gap, respectively. The volume of the emitter being inserted forces or pushes air present in the packaging container to flow out of the packaging container, i.e. a flow is created in the gap between the emitter and the packaging container. When instead pulling the emitter out of the packaging container an inflow of medium is created into the packaging container. The inflow compensates for the volume of the emitter leaving the packaging container, i.e. when the emitter leaves the packaging container air is naturally being sucked into the packaging container from outside causing a flow in the gap between the packaging container and the emitter. It goes without saying that the aforementioned inflow would be created in the same way when the emitter does not move and the packaging container is moved away from the emitter. In the same way, an outflow is created when the emitter does not move and the packaging container is moved towards (and pulled over) the emitter. Since the package is light and the emitter is heavy and has a fragile electron exit window many applications is designed such that it is the package that is moving towards and away from the emitter, while the emitter itself is stationary.

In one or more embodiment, during a movement from the second to the first position, the flow of sterile gaseous medium is configured to be controlled such that a volume of sterile gaseous medium is added, through the outlet such that the opening of the packaging container and the emitter portion at least remain within the local aseptic zone.

In one or more embodiments the emitter is sterile and the sterilization of the interior surface of the packaging container is performed during a relative movement between the emitter and packaging container, from the first to the second position, at so called run-in. In general, when having a sterile emitter it is important to avoid risk for re-infection of the emitter due to the un-sterile packaging container. Therefore, only the run-in is used for sterilization. Run-out (movement from the second to the first position) is considered wasted from a sterilization point of view. To obtain efficient sterilization and to use as short time as possible it is advantageous to make the time-span for run-in as long as possible out of the total available time or at least longer than the time span for run-out. However, a quick run-out will cause extensive inflow of medium into the packaging container. This problem is solved by the invention, and a quick movement from the second to the first position can be accomplished still eliminating risk of re-infection.

In one or more embodiments the device is adapted to control a movement from the first to the second position such that any unsterile gaseous medium flowing from inside the packaging container in a direction towards the opening is sterilised by the cloud, thus maintaining the local aseptic zone around the emitter portion.

In one or more the local aseptic zone is formed along an axis, and the emitter and the packaging container are adapted to move relatively to each other along the axis.

In one or more embodiments the device comprises a plate in a plane perpendicular to the axis. In one or more embodiments the plate defines one rim of the local aseptic zone. The plate may be orientated parallel, perpendicular or angular according to the axis. In one or more embodiments the plate is round. In one or more embodiments the plate is circular. Of course, the plate can have another design such as rectangular, angular, polygonal or the like. The plate comprises the at least one outlet, and the at least one outlet is preferably basically ring-shaped. In one or more embodiments the outlet is instead round or circular. In other words, the nozzle of the outlet is preferably ring-shaped. However, one outlet could also comprise a plurality of nozzles that are arranged in a ring, a grid or the like. The nozzles that belong to the same outlet are controlled or driven, respectively, in the same way. However, different nozzles could also belong to different outlets so that the flow of the gaseous medium that comes out of the nozzles can be adjusted separately by adjusting the different outlets via the appropriate piping systems. Advantageously, the ring-shaped, round or circular design enables a basically cylindrical form of the zone, wherein the cylinder preferably extends along the axis. In the following, the term "outlet" is also used in the same way as the term "nozzle", although "nozzle" means strictly speaking only the orifice.

In one or more embodiments the outlet(s) is/are adapted to guide the flow of the medium along different angles according to the axis. If the axis is a centreline of the plate, the flow of the medium that comes out of the nozzles can preferably be directed towards the axis or centreline, respectively. It can also be directed away from the axis or centreline or basically parallel to them. Different outlets or nozzles with different adjustments or outflow-angles, respectively, are adapted to generate a very consistent and smooth zone. In particular, the outlet(s) is/are adapted to provide a laminar flow in the zone or the laminar flow forms the zone, respectively. In general, the zone can be created using one (big) outlet or nozzle, respectively, as for example a ring-shaped nozzle. However, the zone can also be created using small outlets or nozzles, respectively that are located in different positions.

In one or more embodiments the device comprises at least one guide element that is adapted to guide the sterile gaseous medium along the axis, such that the local aseptic zone can be extended along the axis.

In one or more embodiments at least one outlet is adapted to direct the flow of the medium basically towards the guide element. This can create a vortex or whirls that are adapted to support the formation of a solid, durable and smooth zone along the axis. In one or more embodiments the guide element has a constant cross section that is preferably round, circular, oval, polygonal or angular.

In one or more embodiments the guide element is connected to the plate, and the guide element is preferably located in the center of the plate. In one or more embodiments the cross section of the guide element stays basically constant along the axis. An extension of the zone along the axis is advantageously basically as long as the guide element which extends along the axis. When a packaging container is engaged with the emitter portion the local aseptic zone extends to the opening of the packaging container, however the flow of sterile gaseous medium can extend further down the outer side of the packaging container, but not being part of the aseptic zone. In general, the extension of the local aseptic zone along the axis depends on a speed of the flow of the medium that comes out of the outlets. It depends also on the ambient conditions, for example the pressure or the speed of the ambient medium that surrounds the zone.

In one or more embodiments the guide element is either part of the emitter, or arranged on the emitter.

In one or more embodiments the guide element comprises an outer surface. The outer surface comprises at least one groove that is adapted to guide the medium along the axis.

In one or more embodiments the device comprises a pipe that is adapted to limit the outer diameter of the local aseptic zone. The pipe is preferably attached to the plate. The pipe secures that all air that is around the opening of the packaging container is aseptic. The result is that all air that is sucked into the packaging container is air from the local aseptic zone meaning that only sterile air will enter into the package. In particular, the pipe works as a protection shield. In a preferred embodiment, a plurality, for example 8-13 emitters are arranged at a rotating carousel. The rotation of the carousel can in some applications disturb the building of the local aseptic zone. However, the pipe helps to protect the formation of the zone despite the rotation of the carousel.

The invention also relates to a method for sterilization of the interior surface of packaging containers with electron beam. The method comprises the step of providing an emitter provided with an electron exit window, said emitter being adapted to emit charge carriers, such as electrons, through the electron exit window. Said electrons form an electron cloud. The method further comprises the steps of: providing at least one outlet adapted to provide a flow of sterile gaseous medium, and maintaining, by means of said flow, a local aseptic zone around at least an emitter portion including the electron exit window, thus preventing any flow of medium from outside the local aseptic zone from coming into the local aseptic zone.

In one or more embodiments the method comprises the step of providing a relative movement between the emitter and the packaging container such that the emitter portion is adapted to be temporarily positioned inside the packaging container via an opening, and adapting the local aseptic zone to include the opening at least during said relative movement.

In one or more embodiments the method comprises the step of moving the emitter and the packaging container relatively to each other between first and second positions. The first position is a position in which the packaging container and the emitter are not engaged with each other, and wherein the second position is a position in which the emitter portion is fully inserted into the packaging container for sterilization of the interior surface of the packaging container.

In one or more embodiments the method comprises the step of moving from the second to the first position, and during that movement, controlling the flow of sterile gaseous medium such that a volume of sterile gaseous medium is added, through the outlet, so that the opening of the packaging container and the emitter portion at least remain within the local aseptic zone.

In one or more embodiments the method comprises the step of controlling a movement from the first to the second position, such that any unsterile gaseous medium flowing from inside the packaging container in a direction towards the opening is sterilised by the cloud, thus maintaining the local aseptic zone around the emitter portion.

In one or more embodiments the device is arranged in an irradiation chamber in a filling machine, which filling machine also comprises at least one filling station for filling content into the packaging container, and at least one station for sealing the opening after filling. For example, a plurality of emitters can be provided on a carousel or the like which is adapted to rotate (see for instance the international publication No. WO2014/095838 filed by the applicant). The packaging containers, which are transported for example via a conveyor, reach the carousel and are aligned with one of the (rotating) emitters. During at least a part of one rotation of the carousel, the interior sterilization takes place. The packaging container is lifted to surround the emitter and then lowered again, i.e. the relative movement takes place. The lifting is performed by lifters provided in the conveyor. After the inside sterilisation the packaging container leaves the carousel by means of the conveyor. Therefore, dependent on the size of the carousel, the number of the emitters arranged at the carousel and/or the rotation speed of the carousel, a certain span of time for sterilization is available.

The method according to the invention can include the features and advantages of the electric machine according to the invention and vice versa.

Additional advantages and features of the current invention are shown in the following description of preferred embodiments of the current invention with reference to the attached drawings. Single features or characteristics of respective embodiments are explicitly allowed to be combined within the scope of the current invention.

Figure 1:
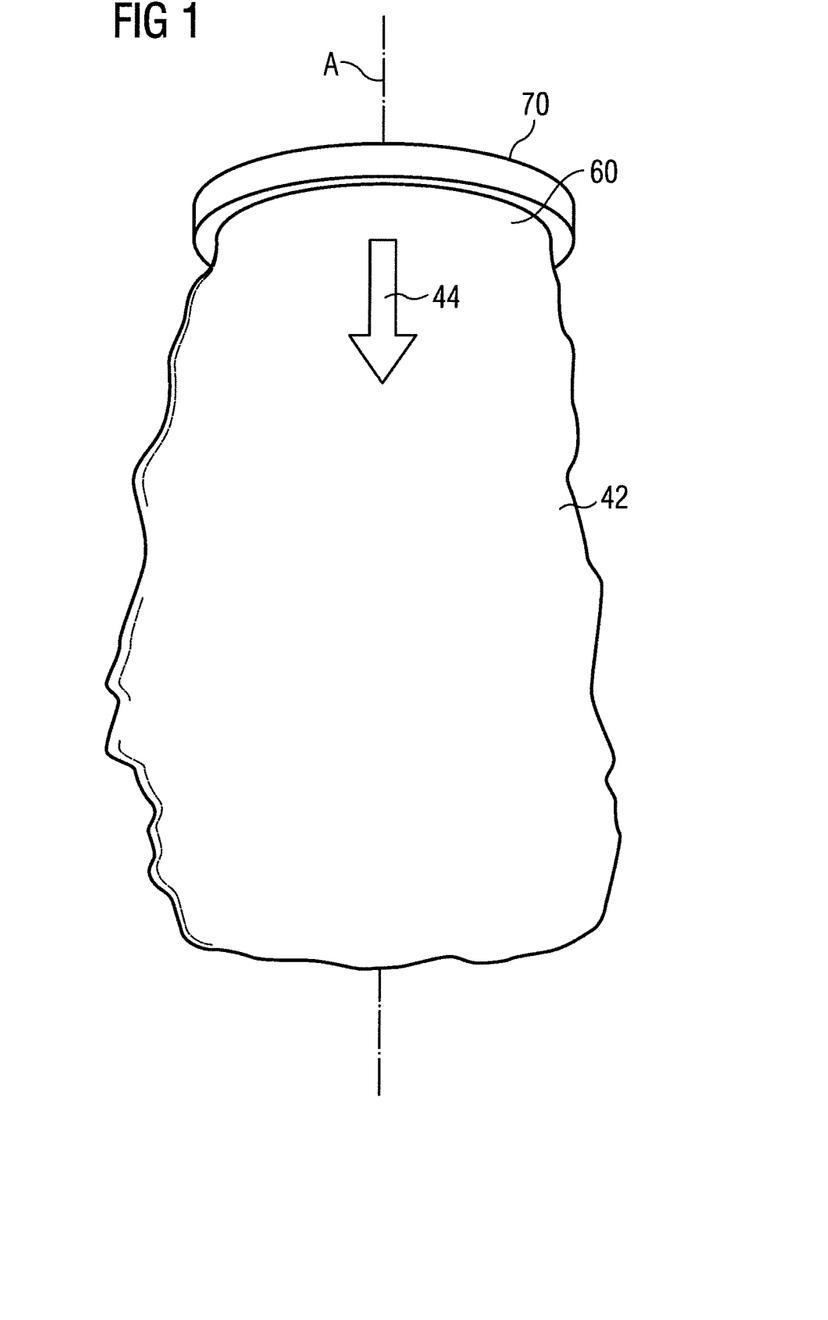
FIG. 1: shows schematically a part of the device according to a first embodiment.

Referring now to FIG. 1, a part of the device is shown. It is a plate 70 that comprises a basically circular outlet 60. The outlet 60 is adapted to provide a flow 44 of a gaseous medium, in particular sterile air or sterile nitrogen. At least part of the flow 44 of the medium is adapted to form a local aseptic zone 42 along a centre axis A.

Figure 2A:
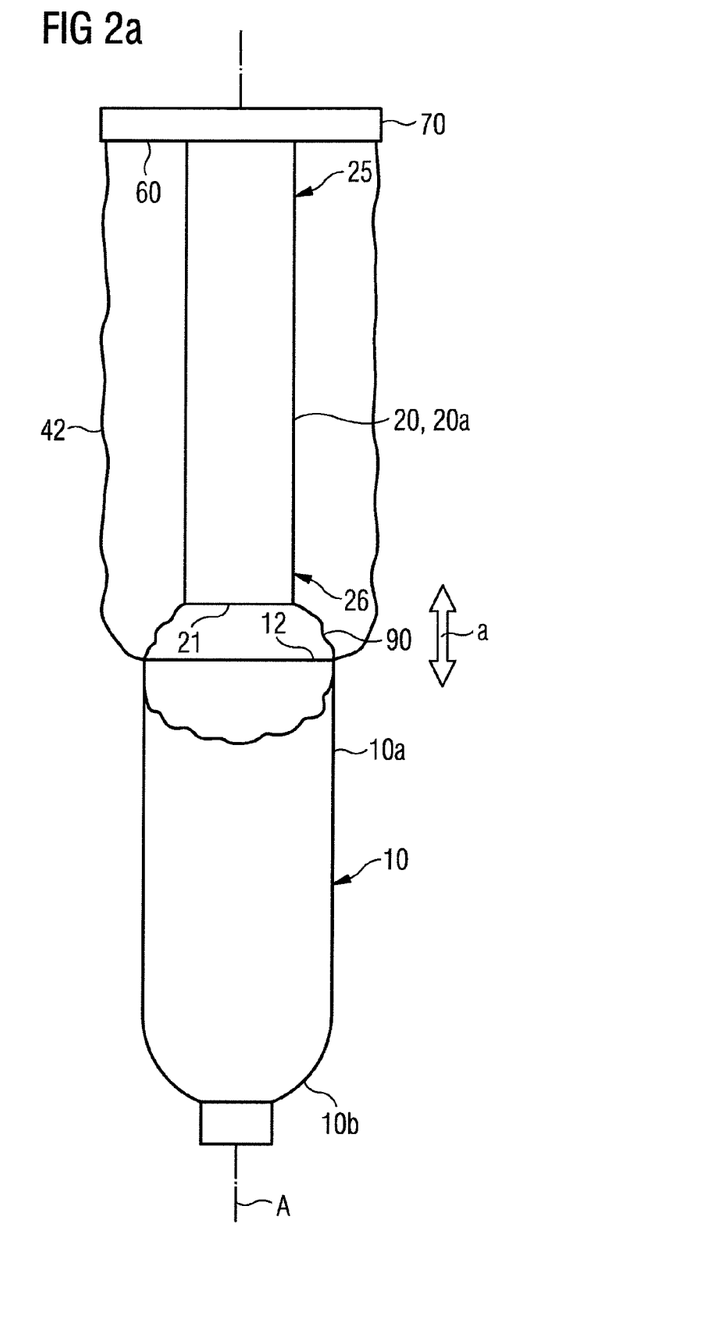
FIG. 2a: shows a first embodiment of the device together with a packaging container, the packaging container and an emitter being in a first position.
Figure 2B:
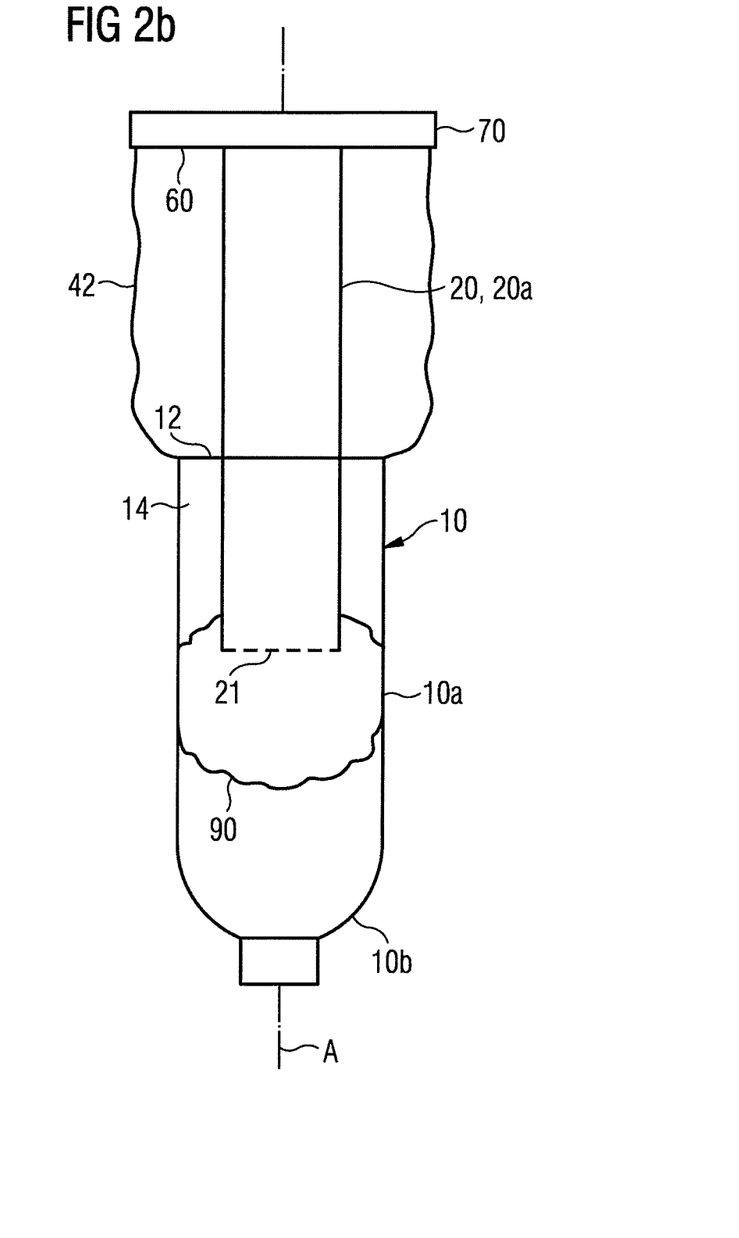
FIG. 2b: shows the first embodiment, the packaging container and the emitter being in a position in between the first and second position.
Figure 2C:
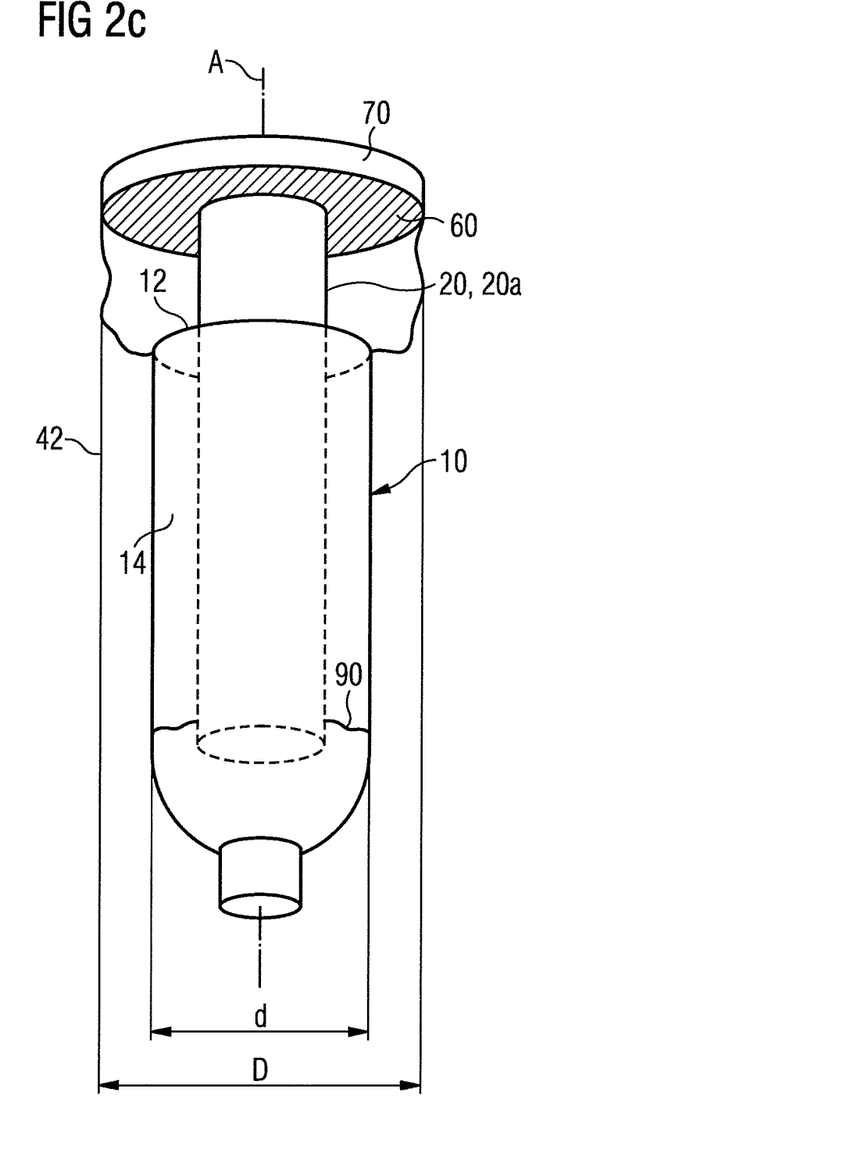
FIG. 2c: shows the first embodiment, the packaging container and the emitter being in a second position.

FIGS. 2a-2c show a first embodiment of a device according to the invention. The device is aimed for interior sterilization of packaging containers 10 using electron beam. The packaging containers 10 are basically tube-shaped and comprises an opening 12. In particular, the packaging container 10 is in a shape ready to be filled with product through the opening 12. It comprises a sleeve body 10a and a top portion 10b. The top portion 10b comprises a neck or spout sealed with a screw cap or other type of closure. The sleeve body 10a is provided with the opening 12. In this embodiment the opening 12 of the packaging container 10 is an open bottom end, which after filling will be sealed and folded to form a substantially flat bottom surface.

Firstly, the device comprises an emitter 20. The emitter 20 comprises an electron exit window 21 and is adapted to emit charge carriers or electrons, respectively, to sterilize at least an inside of the packaging container 10. The electrons form an electron cloud. 90.

In the following an exemplary emitter 20 for sterilizing the interior of this ready-to-fill packaging container 10 will be briefly described.

The emitter 20 comprises an electron generator for emitting a substantially circular electron beam along a path. The electron generator is enclosed in a hermetically sealed vacuum chamber. Said vacuum chamber is provided with an electron exit window 21.

The electron generator comprises a cathode housing and a filament. In use, an electron beam is generated by heating the filament. When an electrical current is fed through the filament, the electrical resistance of the filament causes the filament to be heated to a temperature in the order of 2000° C. This heating causes the filament to emit a cloud of electrons. The electrons are accelerated towards the electron exit window by means of a high-voltage potential between the cathode housing and the exit window (being the anode). Subsequently, the electrons pass through the electron exit window 21 and continue towards the target area, i.e. in this case the inside of the packaging container 10.

The filament can be made of tungsten. A grid may be placed between the filament and an electron beam exit window. It is provided with a number of openings and is used for diffusing the electron beam into a more uniform beam, and for focusing the electron beam towards the target area.

The high-voltage potential is created by for example connecting the cathode housing and the filament to a power supply and by connecting the vacuum chamber to ground. The emitter 20 is generally denoted low voltage electron beam emitter if the voltage is below 300 kV. In one or more embodiments the accelerating voltage is in the order of 90-110 kV. In one or more embodiments the voltage is 100 kV. This voltage results in a kinetic (motive) energy of 100 keV in respect of each electron. However, another voltage can be chosen, for example in the interval 75-150 kV.

By applying an electrical potential also to the previously mentioned control grid the emission of electrons may be further controlled. If a separate and variable electrical potential is applied to the control grid it makes it possible to use the control grid for active shaping of the generated electron beam. For these purposes the control grid may be electrically connected to a separate power supply.

The emitter 20 is, as mentioned, further provided with an electron exit window 21. The window 21 can be made of a metallic foil, such as for example titanium, and can have a thickness in the order of 4-12 μm. A supporting net (not shown) formed of aluminum or copper supports the foil from inside the vacuum chamber. The electrons are exiting the vacuum chamber through the exit window 20.

Figure 3:
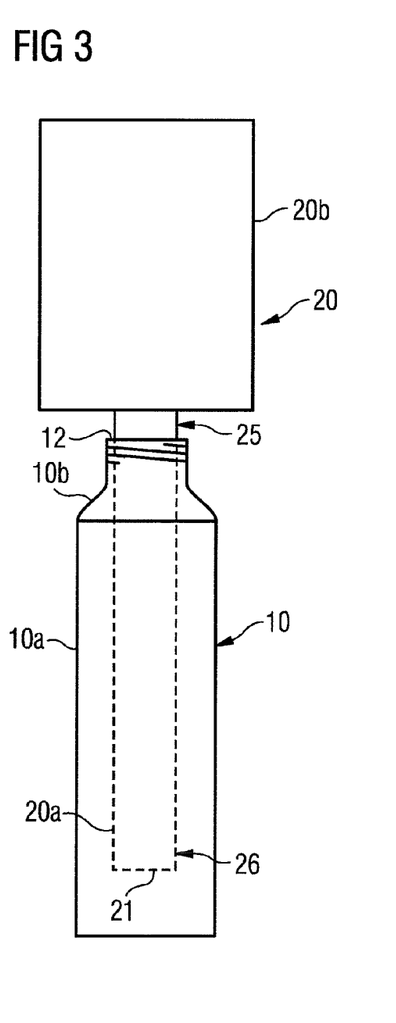
FIG. 3: shows schematically an alternative packaging container and an emitter.

The vacuum chamber may, as shown in for example FIG. 3, be made up of two elongate cylindrical bodies 20a, 20b with substantially circular cross sections. The cylindrical bodies have a common longitudinal centre axis A. The first cylindrical body 20a, or emitter portion 20a, has a first end 25 and a second end 26. The first end 25 connects to the second cylindrical body 20b, i.e. the rest of the emitter, whereas the second end 26 comprises an end surface, in a plane being perpendicular to the centre axis, being provided with the electron exit window 21. The electron exit window 21 is circular and preferably extends over most of the end surface. The diameter of said first body 20a is small enough to be inserted into the ready-to-fill packaging container 10, the cross section of said first body is dimensioned such that it can be guided through the opening 12 of the packaging container 10. The second body 20b is provided with the electron beam generator, and the diameter of said second body 20b is larger than the first body 20a. The diameter of the emitted electron beam, while still inside the emitter 20, is smaller than the diameter of the first body 20a.

Figure 4:
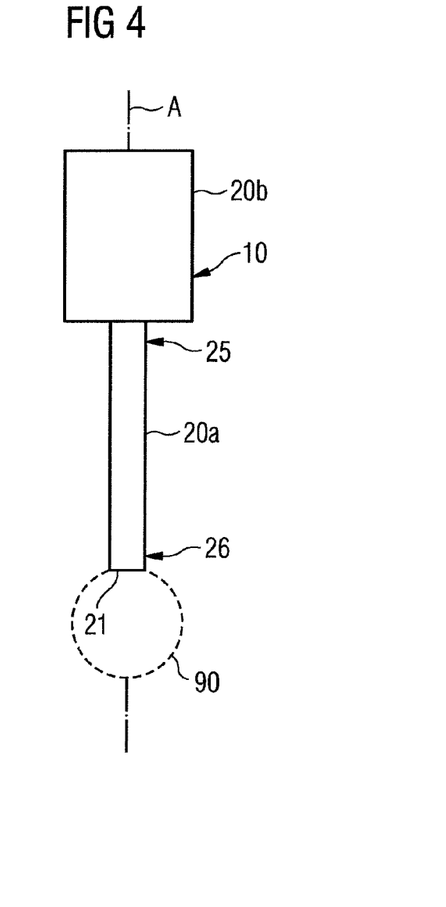
FIG. 4: shows schematically a packaging container and an emitter.

The emitter 20 emits, from its electron exit window 21, the electron cloud 90 illustrated schematically by a line in FIG. 4. The cross sectional shape is somewhat circular, as shown, or droplet-shaped. The shape of the electron cloud is defined by the shape of the electron exit window 21 and by the Brownian motion of individual electrons leaving the electron exit window. The electron cloud is axis-symmetrical, around axis a, and the cloud volume is thereby spherical (or droplet-shaped). The dose rate at the boundary of the electron cloud 90 is approx. 1000-1600 kGy/s. In the centre of the electron cloud 90 the dose rate is higher. The energy of the emitter 20 needs to be matched with the sterilization time available, the packaging container size and shape, the packaging container velocity relative the electron beam emitter, and the above number should be seen purely as an example.

In FIG. 2a only the cylindrical portion 20a of the emitter 20 is shown. From FIG. 2a it is further shown that the device of the invention also comprises a plate 70 with an outlet 60, similar to the plate described in relation to FIG. 1. The first cylindrical portion 20a of the emitter is arranged in the centre of the plate 70, and the plate 70 is arranged in a plane perpendicular to the axis A. Different from the outlet of FIG. 1, the outlet in FIG. 2a is basically ring-shaped. The diameter of the plate and the outlet is larger than the first cylindrical portion 20a of the emitter. Hence, the sterile gaseous medium will flow along the first cylindrical portion 20a of the emitter 20 and surround it.

As mentioned in the summary the sterilization of the interior surface of the packaging container is performed while the packaging container 10 and the emitter 20 are moved relatively to each other. The relative movement is made along axis A and is illustrated by arrow a in FIG. 2a. During the relative movement the emitter portion provided with the electron exit window 21, i.e. the first cylindrical portion 20a, is temporarily positioned inside the packaging container via the opening 12. The relative movement is made between first and second positions. FIG. 2a shows the first position, which is a position in which the packaging container 10 and the emitter 20 are not engaged with each other. The emitter is located above the opening 12 and the cloud 90 fills the opening 12. The second position is a position in which the emitter portion is fully inserted into the packaging container 10 through the opening 12. This position is shown in FIG. 2c. The electron cloud 90 then fills the entire top portion 10b of the packaging container, i.e. the volume farthest away from opening 12. During a sterilization cycle, i.e. during sterilization of a packaging container, movement is performed from the first position to the second position, and from the second position back to the first position.

A movement from the first to the second position, i.e. a relative movement of the emitter and the packaging container towards each other along axis A, will naturally cause an outflow of gaseous medium in a gap 14 between the emitter and the packaging container 10. Gaseous medium in the packaging container will flow out of the packaging container. A movement from the second position to the first position, i.e. a relative movement of the emitter and the packaging container away from each other along axis A, will naturally cause an inflow of gaseous medium in the gap between the emitter and the packaging container. Gaseous medium from outside will flow into the packaging container.

In an application where the emitter is sterile measures need to be taken in order to control the inflows and outflows in the gap, especially not to re-infect the emitter portion 20a. In addition, when the packaging container interior sterilization has begun, any uncontrolled inflow of un-sterile medium should be avoided not to re-infect a sterilized volume inside in the packaging container 10.

In this and the following embodiments the actual sterilization of the inside surface of the packaging container 10 is made during a movement from the first position to the second position, and hence, as mentioned above, the object of this invention is to maintain a local aseptic zone to protect the emitter and the sterilized volume in the packaging container 10, in order to control any potential inflow to avoid re-infection.

It should of course be understood that the emitter may be in continuous operation, and as such it is of course also irradiating the packaging container during movement from the second to the first position. However, not to risk re-infection of the emitter, the dose given when moving from the first to the second position need to be high enough to perform the sterilization on its own.

In the following, the sterilization cycle will be described. The sterilization cycle starts with a movement from the first to the second position. The first position shows in FIG. 2a. The emitter is stationary along axis A and the packaging container is the lifted, upwards in the figure, to surround the emitter. The lifting may be accomplished by a packaging container lifter. During this lifting the inside surface of the packaging container will be sterilized. The pace should be slow enough such that sterilization of the packaging container surface is performed, but also such that the outflow of air from the packaging container 10, due to the insertion of the emitter 20, is sterilized when passing into the electron cloud 90. As such the outflow doesn't risk re-infecting the emitter portion 20a and the already sterilized surface of the packaging container 10. The local aseptic zone 42 is maintained.

FIG. 2b shows a state in which the packaging container 10 has been lifted about half way towards the second position. The interior surface of the upper half of the packaging container is now sterilized, and as the lifting continues more and more of the interior surface is sterilized. In FIG. 2c the second position has been reached, the electron cloud 90 fills the entire top portion 10b and the entire interior surface has been sterilized.

In a next step the packaging container 10 will start to be lowered from its position around the emitter 20. Simultaneously the flow of sterile gaseous medium provided from the outlet 60 maintains the aseptic zone 42. A description of the aseptic zone 42 will follow.

In a final step of the sterilization cycle the packaging container 10 has been lowered so much that the emitter 20 is no longer inside the packaging container 10. The first position has been reached again, see FIG. 2a. The electron cloud 90 still protects the opening 12 of the packaging container 10, and the packaging container 10 can for example be moved into an overlapping electron cloud of other emitters provided for sterilization of the outer surface of the packaging container.

As mentioned above, the object of this invention is to maintain a local aseptic zone 42 to protect the emitter 20 and the sterilized packaging container 10. In the following this will be described.

When the emitter 20 is quickly leaving the packaging container 10, i.e. when the packaging container is lowered from the emitter, there can be created an inflow of medium from outside the packaging container to fill the volume left by the emitter. Since the packaging container and the emitter are sterile this inflow would only be acceptable if it is sterile. The flow 44 (FIG. 1) of sterile gaseous medium from the outlet 60 above the packaging container provides for a sterile inflow. In addition, the flow 44 is controlled such that the volume of sterile gaseous medium that is added will make sure that the opening 12 of the packaging container 10 and the emitter portion 20a will at least remain within the aseptic zone 42. This can be accomplished in that a volume of sterile gaseous medium is added, per time unit, to at least compensate for the volume of a portion 20a of the emitter 20 leaving the packaging container 10 during the same time. This means that the flow of sterile gaseous medium prevents unsterile medium from coming into contact with the emitter portion 20a and the packaging container opening 12, and that any medium entering into the packaging container and comes into contact with the emitter portion 20a is sterile. Hence, the flow 44 (FIG. 1) of sterile gaseous medium balances the local aseptic zone 42 such that the zone will still be capable of including the packaging container opening 12 and encapsulating the emitter portion 20a.

In more detail this means that the local aseptic zone 42 has a diameter D (FIG. 2c) being larger than the outer diameter d of the opening 12 of the packaging container 10. In addition, the emitter portion 20a, which has basically a constant circular cross section, has a diameter smaller than the diameter of the packaging container 10. As a consequence, the local aseptic zone 42 is formed around at least the opening 12 of the packaging container 10. The length of the zone along axis A varies. When there is a packaging present the length is large enough to include the opening of the packaging container. When there is no packaging container engaged with the emitter, the length is large enough to encapsulate the emitter portion 20a, i.e. the length extends at least to the cloud 90. The flow 44 of sterile gaseous medium may extend longer, especially in the state when a packaging container 10 is engaged with the emitter portion 20a. The flow 44 may be extended along the outer side of the packaging container, but since the outer surface of the packaging container is not sterile, the outer surface cannot be considered part of the aseptic zone 42. The flow 44, being directed downwards, from the opening of the packaging container and down towards the other end of the packaging container, will however make sure that there is not created any flow upwards along the packaging container 10, towards the aseptic zone 42.

Figure 5:
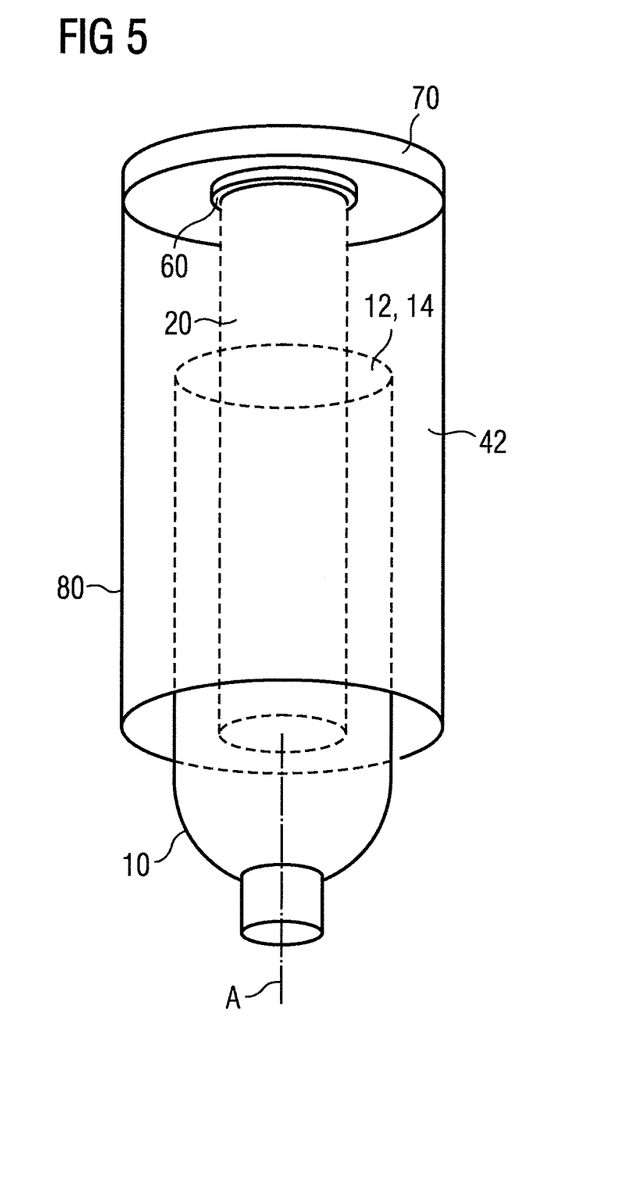
FIG. 5: shows a second embodiment of the invention together with a packaging container.

FIG. 5 shows a second embodiment of a device for creating a local aseptic zone 42. The embodiment shown in FIG. 5 is similar to the one shown in FIGS. 4a-c, however an outlet 60 is much thinner. The outlet 60 is located next to a hole in the plate 70 through which the emitter 20 extends. In addition, a pipe 80 is attached to a plate 70. The pipe is attached at the outer perimeter of the plate, and the pipe has a diameter the same as the diameter of the plate. The pipe 80 helps stabilizing the local aseptic zone 42. The pipe 80 is the outer boundary of the aseptic zone, and the flow should be controlled such that the volume inside the pipe 80 is always filled with sterile medium from the outlet 60. The pipe 80 of this embodiment may of course also be combined with the embodiment of FIG. 4a-c.

Figure 6:
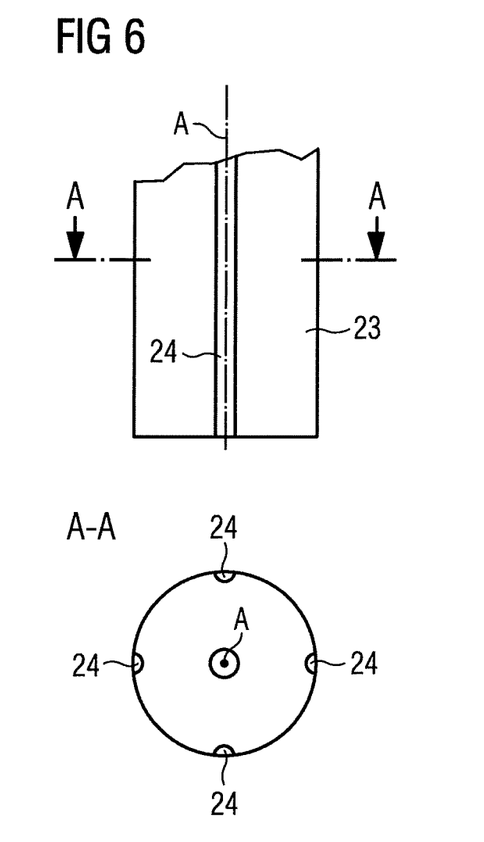
FIG. 6: shows a guide element of the invention.

FIG. 6 shows a guide element 23 which may be combined with the devices of any the described embodiments. The guide element 23 is adapted to guide the sterile gaseous medium along the axis A such that the local aseptic zone 42 can be extended, or prolonged, along the axis A. It helps the flow of sterile gaseous medium reach longer, and better keep the direction, and stay closer to the emitter portion 20a. The guide element 23 is either part the emitter 20, for instance the guide element 23 is the outer surface of the emitter portion 20a. Alternatively, it is a pipe or similar being arranged on or attached to the emitter portion 20a, preferably surrounding the outer surface of the emitter portion 20a. The guide element 23 comprises an outer surface comprising at least one groove 24 that is adapted to guide the medium along the axis A. In the embodiment shown there are four straight grooves extending in parallel with axis A. A section view A-A shows a cross-section of the guide element.

Figure 7:
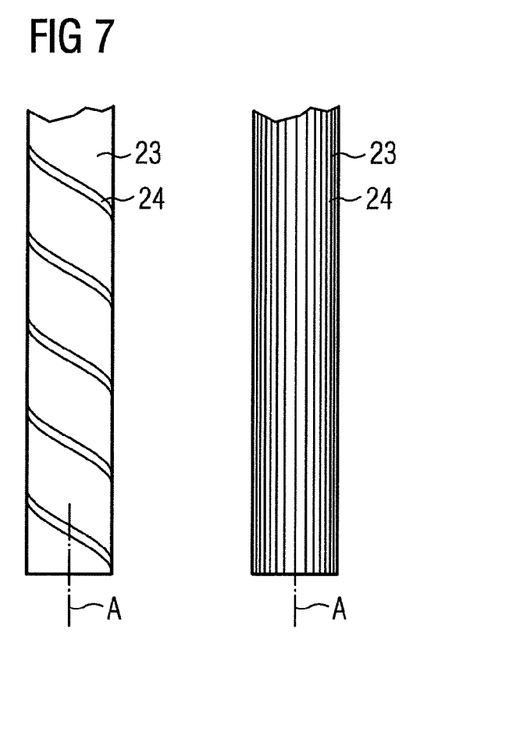
FIG. 7: shows another two guide elements of the invention.

FIG. 7 shows another two embodiments of the guide elements 23. In the left embodiment a groove 24 is spirally formed along the guide element 23. In the right embodiment a plurality of grooves is formed in parallel with the axis A.

Figure 8:
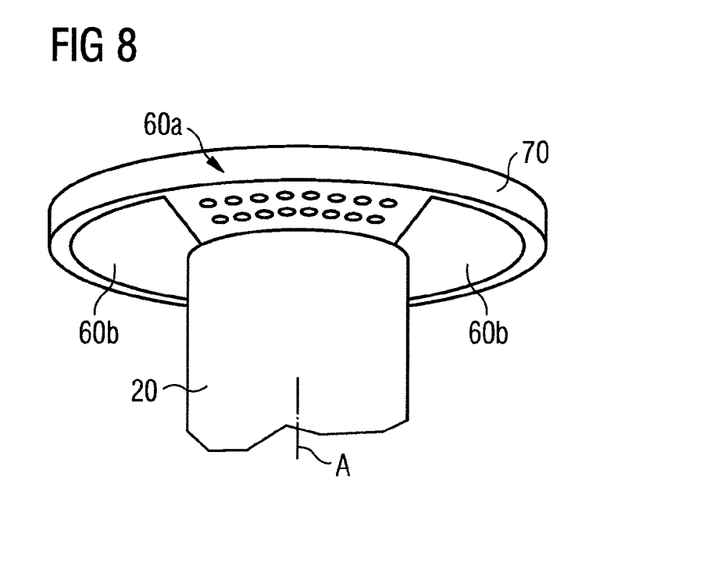
FIG. 8: shows different possibilities for arranging outlets on a plate or a guide element or an emitter, respectively.

FIG. 8 shows a further embodiment of the plate 70 according to the invention. Several small outlets 60a are arranged in one or more sections of the plate 70, and in other sections larger outlets 60b are formed. An emitter 20, with or without guide element, is attached to the plate 70 and extends along an axis A.

Figure 9:
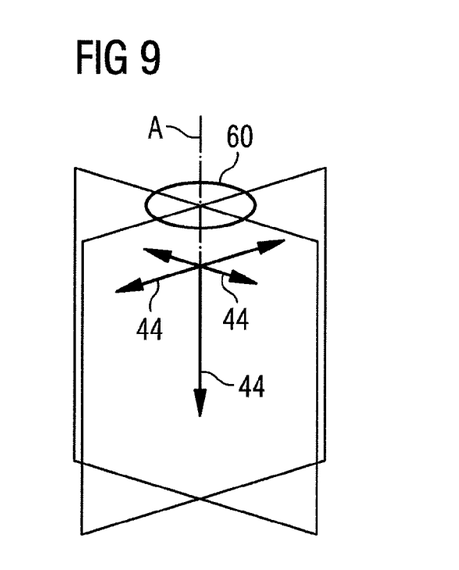
FIG. 9: shows a basic scheme of an outlet that is adapted to guide a flow of a medium along different directions.

FIG. 9 shows a basic scheme of an outlet 60 wherein different flow directions of a flow 44 are visualized by the different arrows. The arrows reveal that different flow directions can be established out of the outlet 60. It goes without saying that the flow 44 does not have to be directed strictly along the arrows. All intermediate directions are also possible.

Figure 10:
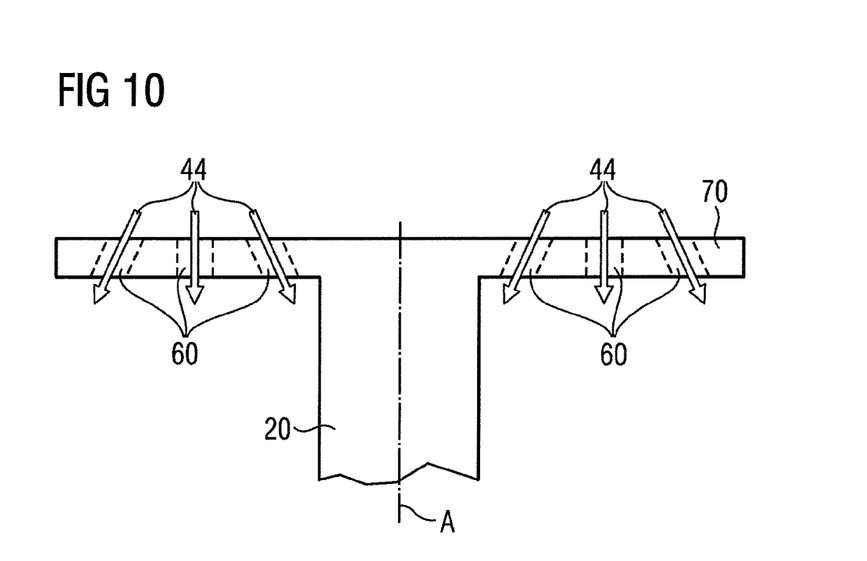
FIG. 10: shows a further embodiment of a plate with a plurality of outlets.

FIG. 10 shows a plate 70 comprising a plurality of outlets 60. According to an axis A that extends basically along an emitter 20, the flows 44 of the medium out of the outlet 60 have different directions.

The device according to the invention can be arranged in an irradiation chamber in a filling machine. The filling machine comprises at least one filling station for filling content into the packaging container and at least one station for sealing the opening after filling. The invention can for example be applied in the sterilization device as described in the international publication No. WO2014/095838 filed by the applicant. During interior sterilization of the packaging containers a relative movement is made between the packaging container and the emitter. A plurality of emitters are provided on a carousel or the like which is adapted to rotate. The packaging containers, which are transported for example via a conveyor, reach the carousel and are attached to one of the (rotating) emitters. During at least a part of one rotation of the carousel, the sterilization takes place and the packaging container is removed from the appropriate emitter or from the carousel, respectively.

Figure 11:
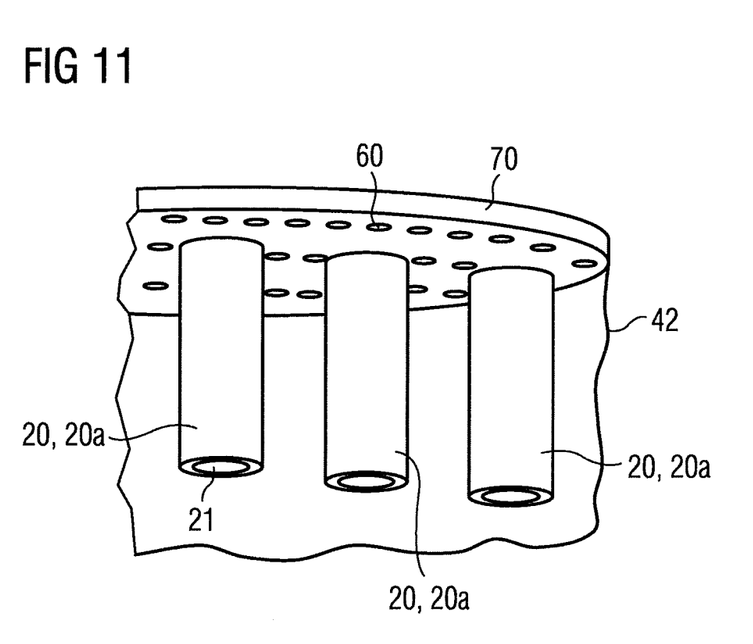
FIG. 11: shows further embodiment of a plate with a plurality of guide elements and/or emitters, respectively.

FIG. 11 shows another embodiment in which the plate 70 is in fact the carousel mentioned above, i.e. a carousel provided with several emitters 20. The plate 70 comprises a plurality of outlets 60 that are adapted to form a zone 42 that covers at least the emitter portions 20a of the plurality of emitters 20.

In the embodiments described the opening 12 of the packaging container 10 is an open bottom end, which after filling will be sealed and folded to form a substantially flat bottom surface. It should however be understood that this opening 12, through which the emitter 20 is received and through which filling will be made, may instead be arranged in the top portion 10b of the packaging container, as a neck or spout portion of the packaging container 10. FIG. 3 illustrates such. The neck or spout portion will, after filling, be sealed by for instance a screw cap.

An aseptic zone has been described. It should be understood that the outlet and the flow of sterile air can be used, not to maintain an aseptic zone as such, but to merely enable a somewhat more hygienic condition inside an irradiation chamber. Providing sterile air using an outlet of the invention above and around the emitter portion and the opening of the packaging container is advantageous in that it provides for a more controlled environment inside the irradiation chamber. For example, any air flows or turbulence in the irradiation can be better controlled/predicted.

REFERENCE NUMERALS 10 packaging container
10a sleeve body
10b top portion
12 opening
14 gap
20 emitter
20a first cylindrical body
20b second cylindrical body
21 electron exit window
22 outer surface
23 guide element
24 groove
25 first end
26 second end
42 zone
44 flow (of the medium)
60 outlet
70 plate
80 pipe
90 cloud
A axis
a arrow
D outer diameter (of the zone)
d diameter (of the basically tube shaped packaging container)

The invention claimed is:

1. Device for sterilization of the interior surface of packaging containers with electron beam, comprising:
   an emitter provided with an electron exit window, said emitter being adapted to emit charge carriers, such as electrons, through the electron exit window, said electrons forming an electron cloud,
   wherein the device comprises at least one outlet adapted to provide a flow of sterile gaseous medium adapted to maintain a local aseptic zone around at least an emitter portion including the electron exit window, thus preventing any flow of medium from outside the local aseptic zone from coming into the local aseptic zone;
wherein the emitter and the packaging container are adapted to perform a movement relative to each other such that the emitter portion is temporarily inserted into the packaging container via an opening, and
wherein the local aseptic zone is adapted to include the opening of the packaging container at least during the relative movement between the emitter and the packaging container.

2. Device according to claim 1, wherein the emitter portion has a first end connecting to the rest of the emitter and a second end comprising the electron exit window, and wherein the outlet is arranged such that the sterile gaseous medium is flowing along the emitter portion in a direction from the first end to the second end.

3. Device according to claim 2,
wherein the local aseptic zone is formed along an axis, and
wherein the emitter and the packaging container are adapted to move relatively to each other along the axis.

4. Device according to claim 3,
wherein the device comprises a plate, in a plane perpendicular to the axis,
wherein the plate comprises the at least one outlet, and
wherein the at least one outlet is preferably basically ring-shaped and provided around the first end of the emitter portion.

5. Device according to claim 4,
wherein the device comprises a pipe that is adapted to limit the outer diameter of the local aseptic zone,
wherein the pipe is preferably attached to the plate.

6. Device according to claim 3,
wherein the outlet is/are adapted to guide the flow of the medium along different angles according to the axis.

7. Device according to claim 3,
wherein the device comprises at least one guide element that is adapted to guide the sterile gaseous medium along the axis, such that the local aseptic zone can be extended along the axis.

8. Device according to claim 7,
wherein the guide element is connected to the plate, and
wherein the guide element is preferably located in the center of the plate.

9. Device according to claim 7, wherein the guide element is either part of the emitter, or arranged on the emitter.

10. Device according to claim 7,
wherein the guide element comprises an outer surface, and
wherein the outer surface comprises at least one groove that is adapted to guide the medium along the axis.

11. Device according to claim 1,
wherein the emitter and the packaging container are adapted to perform the movement relatively to each other between first and second positions,
wherein the first position is a position in which the emitter is outside the packaging container, and
wherein the second position is a position in which the emitter portion is fully inserted into the packaging container, through the opening of the packaging container, for sterilization of the interior surface of the packaging container.

12. Device according to claim 11, wherein, during a movement from the second to the first position, the flow of sterile gaseous medium is configured to be controlled such that a volume of sterile gaseous medium is added, through the outlet such that the opening of the packaging container and the emitter portion at least remain within the local aseptic zone.

13. Device according to claim 11, wherein the device is adapted to control a movement from the first to the second position such that any unsterile gaseous medium flowing from inside the packaging container in a direction towards the opening is sterilised by the cloud, thus maintaining the local aseptic zone around the emitter portion.

14. Device according to claim 1, wherein the opening of the packaging container is a spout or a bottom of the packaging container.

15. Method for sterilization of an interior surface of a packaging container with electron beam, comprising:
positioning an emitter inside the packaging container via an opening, the emitter including an electron exit window;
emitting charge carriers through the electron exit window to form an electron cloud;
producing a flow of sterile gaseous medium; and
maintaining, by said flow of sterile gaseous medium, a local aseptic zone around at least an emitter portion including the electron exit window and the opening of the packaging container, thus preventing any flow of medium outside the local aseptic zone from coming into the local aseptic zone.

16. Device for sterilizing an interior of a ready-to-fill packaging container, the device comprising:
an emitter that houses a sealed vacuum chamber in which is produced electrons, the emitter including a free end portion configured to be positioned inside the ready-to-fill packaging container and at which is located an electron exit window from which is emitted the electrons while the electron exit window at the free end portion of the emitter is located in the packaging container to form an electron cloud in the packaging container that sterilizes the packaging container;
the emitter and the packaging container being relatively movable so that the emitter moves between one position in which the electron exit window at the free end portion of the emitter is positioned inside the packaging container to an other position in which the electron exit window at the free end portion of the emitter is positioned outside the packaging container;
an outlet configured to be connected to a sterile gaseous medium source so that a flow of sterile gaseous medium exits the outlet to maintain a local aseptic zone around the electron exit window that prevents any flow of medium outside the local aseptic zone from coming into the local aseptic zone; and
the outlet being axially spaced from the electron exit window so that the electron exist window of the emitter is positionable in the packaging container via an opening in the packaging container while the outlet is, at the same time, outside the packaging container;
wherein the local aseptic zone includes the opening of the packaging container at least during the relative movement between the emitter and the packaging container.

17. Device according to claim 16, further comprising a plate connected to the emitter, the outlet being provided in the plate.

18. Device according to claim 16, wherein the emitter possesses a central axis, and the plate lies in a plane perpendicular to the central axis.

19. Device according to claim 16, wherein the emitter possesses a central axis, further comprising a guide element configured to guide the sterile gaseous medium from the outlet along the central axis to extend the local aseptic zone along the central axis.

* * * * *